US00PP13406P3

(12) United States Plant Patent
Goemans

(10) Patent No.: US PP13,406 P3
(45) Date of Patent: Dec. 24, 2002

(54) ALSTROEMERIA PLANT NAMED 'ISADORA'

(75) Inventor: Robert Adrian Goemans, Chichester (GB)

(73) Assignee: Wulfinghoff Alstroemeria B.V., Rijswijk (NL)

( * ) Notice: Subject to any disclaimer, the term of this patent is extended or adjusted under 35 U.S.C. 154(b) by 0 days.

(21) Appl. No.: 09/804,236

(22) Filed: Mar. 13, 2001

(65) Prior Publication Data

US 2002/0133857 P1 Sep. 19, 2002

(51) Int. Cl.[7] ..... A01H 5/00
(52) U.S. Cl. ..... Plt./309
(58) Field of Search ..... Plt./309

(56) References Cited

U.S. PATENT DOCUMENTS

PP10,836 P * 3/1999 van Andel ..... Plt./309
PP11,688 P * 12/2000 van Andel ..... Plt./309

OTHER PUBLICATIONS

GTITM UPOVROM Citation for 'Isabel' as per PL NLI ALO0032; Dec. 12, 1990.*

GTITM UPOVROM Citation for 'Isabel' as per PL PBR ALO0032; Feb. 5, 1993.*

Przybyla, A.A., Mutagenesis in Creation of New Alstroemeria Genotypes, ACTA Horticulturae; No. 508; Abstract; 2000.*

* cited by examiner

*Primary Examiner*—Kent L. Bell
(74) *Attorney, Agent, or Firm*—Foley & Lardner

(57) ABSTRACT

A new and distinct Alstroemeria plant named 'Isadora' characterized by growth height of 10–30 cm; suitable for pots with a diameter larger than 7 cm; bushy, dwarf growth habit; red flowers, yellow base with black stripes; and 4–6 week inflorescence longevity.

1 Drawing Sheet

GENUS AND SPECIES OF THE CLAIMED PLANT

*Alstroemeria hyrida.*

VARIETY DENOMINATION

'Isadora'.

BACKGROUND OF THE INVENTION

The present invention comprises a new and distinct cultivar of Alstroemeria plant, hereinafter referred to by the cultivar name 'Isadora'.

The new cultivar, 'Isadora' originated by Robert Adrian Goemans from a hybridization made in a controlled breeding program in Chichester in Sussex, United Kingdom. The female parent was an unnamed cultivar of unknown origin (unpatented). The male parent of 'Isadora' was an unnamed selection from a breeding line named Butterfly (unpatented).

'Isadora' was discovered and selected as one flowering plant within the progeny of the stated parentage by Robert Adrian Goemans in 1997 in a controlled environment in Chichester, United Kingdom. The first act of asexual reproduction of 'Isadora' was accomplished when vegetative cuttings were taken from the initial selection in May, 1998, in a controlled environment in Chichester, United Kingdom. Horticultural examination of selected units initiated in 1998, has demonstrated that the combination of characteristics as herein disclosed for 'Isadora' are firmly fixed and retained through successive generations of asexual reproduction.

BRIEF DESCRIPTION OF THE INVENTION

The following traits have been repeatedly observed and are determined to be basic characteristics of which in combination distinguish this Alstroemeria as a new and distinct cultivar:

1. Suitable for pots with a diameter larger than 7 cm;
2. Growth height of 10–30 cm;
3. Bushy, dwarf growth habit;
4. Red flowers, yellow middle with black stripes; and
5. 4–6 week inflorescence longevity.

'Isadora' has not been observed under all possible environmental conditions. The phenotype may vary significantly with variations in environment such as temperature, light intensity and day length, without any change in genotype. The following observations, measurements and comparisons describe plants grown in Chichester, Sussex, United Kingdom under greenhouse conditions which approximate those generally used in commercial practice. 'Isadora' is distinguished from its parental cultivars primarily in flower color.

There are no commercial cultivars known to the present inventor, similar in comparison to 'Isadora'.

BRIEF DESCRIPTION OF THE DRAWINGS

The accompanying photograph shows a typical plant of the new variety with colors as accurate as possible.

Sheet 1 shows the flowers and foliage of 'Isadora'.

DETAILED BOTANICAL DESCRIPTION

In the following description, color references are made to The Royal Horticultural Society Colour Chart (R.H.S.). The color values were determined in the afternoon on Sep. 16, 2000 under normal daylight at Wateringen, The Netherlands. The plants described are nine months of age, and grown in 15 cm pots. The plants asexually propagated by rooted tissue cultured rhizomes.

Plant:

*Form*.—Pot plant.

*Height*.—10–30 cm under Dutch greenhouse conditions.

*Diameter*.—18 cm wide.

*Growth*.—Bushy dwarf growth habit.

*Time it takes to produce a flowering plant*.—From planting rooted tissue cultured rhizomes to flowering: 6 to 9 months, depending on culture conditions.

*Number of lateral branches*.—33 per plant.

*Stem*.—Size: 5 cm in length, 5 mm in diamater. Texture: Firm/fleshy. Color: Yellow-green, RHS 145 D. Length of internode: 3 mm.

*Foliage*.—Quantity: 10–20 leaves on each stem, depending on growth stage. Size of leaf: Length: 35–50 mm. Width: 28–35 mm. Shape of leaf: Oblong-ovate, with obtuse apex and rounded base, margin entire. Texture of leaf: Smooth and firm. Venation: Parallel. Color: Upper side: Dark green RHS 141 A to 141 B. Underside: Light-green RHS 138 A.

*Petioles*.—Size: 5 cm in length, 5 mm in diamater. Color: Yellow-green, RHS 146B.

*Rhizomes*.—Color: White RHS 158 A to 158 D. Size: Length 10–50 mm; diameter 6–15 mm, depending on age.

Inflorescence:

*Bud*.—Form: Tubular pointed. Diameter: 10–20 mm. Length: 15–25 mm. Color: Red RHS 46 A to RHS 46 B.

*Flower*.—Size: Medium, length 40–60 mm; width 40–60 mm. Depth: 55 mm. Borne: Whorl. Shape: Broad obovate. Color: Outer tepals: Red, between RHS 46B and RHS 46C, yellow in the middle, between RHS 12A and RHS 13A (both surfaces). Upper surface of Inner tepals: RHS 178B with yellow, 20A in the middle. Lower surface of Inner tepals: RHS 179B with yellow, 20A in the middle. Other notations: Black stripes on all tepals, upper and lower surfaces, RHS 202 A. Number of flowers per cyme: 3–4. Number of open flowers per plant: Typically 9–12 per 15 cm pot.

*Tepals*.—Outer tepals: Size: 52 mm in length; 32 mm in width. Apex: Retuse. Base: Cuneate. Margin: Entire to serrulate. Texture: Silky. Inner tepals: Size: 54 mm in length; 19 mm in width. Apex: Cuspidate. Base: Cuneate. Margin: Dentate. Texture: Silky.

*Peduncle*.—Length: 3 cm. Color: Medium-green RHS 144 D to 144 B.

*Lasting quality of the bloom*.—On the plant: 21 days; cut flower: 14 days.

*Flowering season*.—May–September under outside conditions.

*Fragrance*.—None.

Reproductive organs:

*Stamens*.—6.

*Pollen*.—Plentiful, yellow, RHS 9 B.

*Anthers*.—Yellow RHS 13 A.

*Filaments*.—Red RHS 42 B to 44 B.

*Pistils*.—1, Red-pink. RHS 50 B to 50 C.

*Stigma*.—Pink-white RHS 36 A to 36 C.

*Seeds*.—None.

Pest/disease resistance/susceptibility: No observations made to date.

I claim:

1. A new and distinct Alstroemeria plant named 'Isadora', substantially as illustrated and decribed herein.

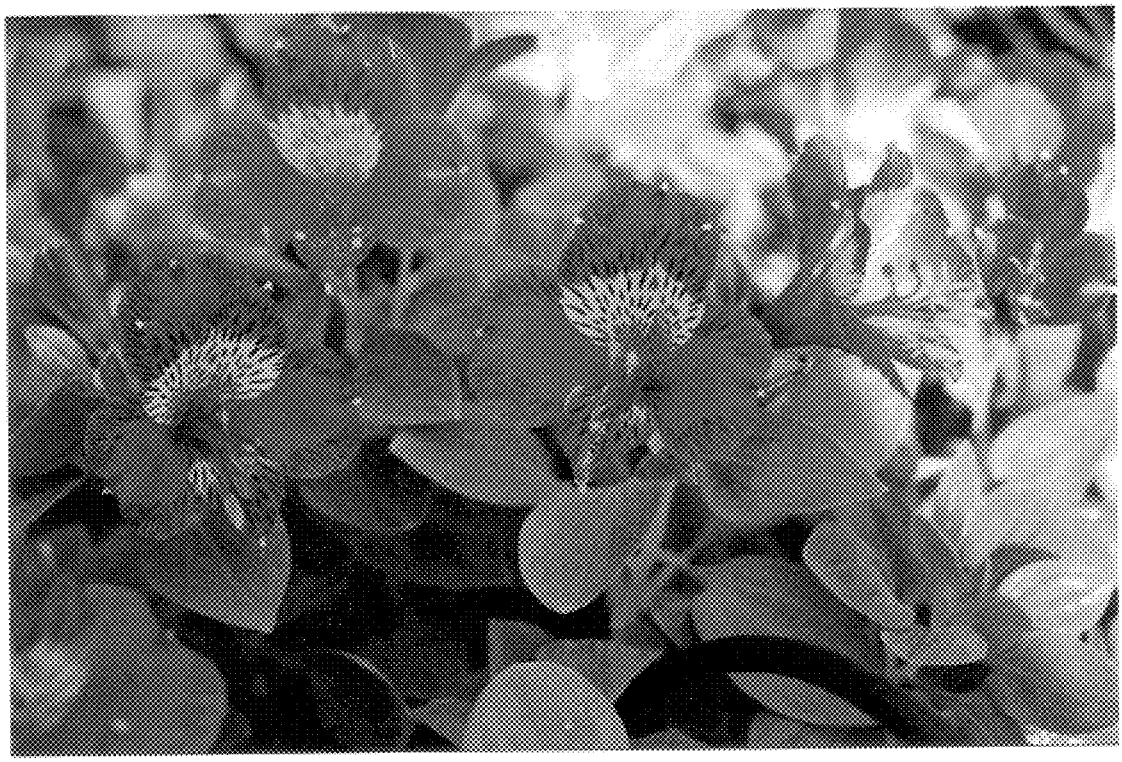

* * * * *